(12) United States Patent
Jeraj et al.

(10) Patent No.: US 12,150,776 B2
(45) Date of Patent: Nov. 26, 2024

(54) SYSTEM AND METHOD FOR MONITORING MULTIPLE LESIONS

(71) Applicants: Wisconsin Alumni Research Foundation, Madison, WI (US); AIQ SOLUTIONS, INC., Madison, WI (US)

(72) Inventors: Robert Jeraj, Madison, WI (US); Victor Fernandes, Madison, WI (US); Timothy Perk, Madison, WI (US); Peter Ferjancic, Madisn, WI (US); Daniel Huff, Madison, WI (US)

(73) Assignee: Wisconsin Alumni Research Foundation & AIQ Solutions, Inc., Madison, WI (US)

( * ) Notice: Subject to any disclaimer, the term of this patent is extended or adjusted under 35 U.S.C. 154(b) by 672 days.

(21) Appl. No.: 17/240,222

(22) Filed: Apr. 26, 2021

(65) Prior Publication Data

US 2022/0338805 A1   Oct. 27, 2022

(51) Int. Cl.
*A61B 5/00* (2006.01)
*G06T 7/00* (2017.01)
*G06T 7/38* (2017.01)

(52) U.S. Cl.
CPC .......... *A61B 5/4842* (2013.01); *G06T 7/0016* (2013.01); *G06T 7/38* (2017.01); *G06T 2207/10104* (2013.01); *G06T 2207/20212* (2013.01); *G06T 2207/30096* (2013.01)

(58) Field of Classification Search
CPC ....... A61B 5/4842; G06T 7/38; G06T 7/0016; G06T 2207/10104; G06T 2207/20212; G06T 2207/30096
See application file for complete search history.

(56) References Cited

U.S. PATENT DOCUMENTS

| | | | |
|---|---|---|---|
| 9,147,242 B2 * | 9/2015 | Kadir | G06T 7/0012 |
| 2010/0250275 A1 | 9/2010 | Sakagawa et al. | |
| 2011/0060602 A1 | 3/2011 | Grudzinski et al. | |
| 2013/0156280 A1 | 6/2013 | Kadir | |
| 2014/0276035 A1 | 9/2014 | Jeraj et al. | |
| 2016/0100795 A1 * | 4/2016 | Jeraj | A61B 5/0035 600/431 |
| 2018/0330495 A1 | 11/2018 | Jeraj et al. | |
| 2020/0085382 A1 | 3/2020 | Taerum et al. | |
| 2021/0154209 A1 * | 5/2021 | Baskin-Bey | A61K 31/635 |
| 2023/0289968 A1 * | 9/2023 | Martinelli | G06T 7/254 |

FOREIGN PATENT DOCUMENTS

KR   20200089146 A   7/2020

OTHER PUBLICATIONS

International Search Report for PCT/US2022/071534 mailed Jul. 27, 2022.

* cited by examiner

*Primary Examiner* — Khai M Nguyen
(74) *Attorney, Agent, or Firm* — Boyle Fredrickson, SC

(57) ABSTRACT

A method and apparatus for tracking disease progression as revealed by multiple lesions perform a global optimization to identify corresponding lesions by overlap, for example, after outlines of the lesions have been morphologically dilated. A clustering algorithm addresses the problem of lesions separating into parts or joining together to provide a clear picture of disease progression.

16 Claims, 3 Drawing Sheets

SYSTEM AND METHOD FOR MONITORING MULTIPLE LESIONS

STATEMENT REGARDING FEDERALLY SPONSORED RESEARCH OR DEVELOPMENT

—

CROSS REFERENCE TO RELATED APPLICATION

—

BACKGROUND OF THE INVENTION

The present invention relates to techniques for assessing disease treatment and in particular for a computerized assessment system providing improved lesion tracking particularly with high numbers or densities of lesions.

Metastasis is the leading cause of cancer-related mortality. In metastasis, cells of a primary cancer break away from where they were first formed and travel through the body to create new lesions. Each metastatic lesion may respond differently to treatment and accordingly lesion-level assessment may be necessary for a complete understanding of disease response. Such lesion assessment, however, is difficult and typically requires manual matching of as many as hundreds of corresponding lesions, a tedious, subjective, and error-prone task.

Medical imaging is an important tool for identifying metastatic lesions and monitoring their progression and therapeutic response. In medical imaging, a contrast agent such as a radioactive isotope having an affinity for disease tissue is injected into the patient and tracked using imaging modalities such as MRI, CT, and/or PET.

The ability to obtain images of lesions has led to the investigation of automatic methods of lesion tracking using such images. In these systems, lesions are automatically identified, for example, by the molecular imaging signatures (e.g., uptake) in different images separated in time. Comparison of these images allows assessment of disease progression and/or the efficacy of the treatment.

U.S. Pat. No. 10,445,878 entitled "Image Enhancement System for Bone Disease Evaluation," assigned to the assignees of the present invention and hereby incorporated by reference, describes a lesion tracking system for tumors present in the skeletal system, the latter of which presents an articulated but rigid target simplifying the registration of longitudinally acquired images. A more general lesion tracking system for metastatic lesions spread across the entire patient anatomy remains difficult.

SUMMARY OF THE INVENTION

The present inventors have identified important deficiencies in current approaches to automatic lesion tracking that limit its broad applicability to lesion tracking including (1) a failure to accommodate high lesion density that can produce multiple or ambiguous overlapping of lesions in successive images and (2) a failure to properly account for or distinguish lesions that split, merge, appear, or disappear. The present invention addresses this former problem through an optimization based on conformally dilated areas around the lesions that better identifies corresponding lesions in later images. The mutability of the lesions over time is addressed through a clustering process informed by characteristic irregularities in the tumor outlines.

In one embodiment, the invention provides an apparatus for assessing cancer treatment of a patient employing an electronic computer executing a stored program to:
(a) receive a first and subsequent second scan of tissue of the patient revealing diseased tissue;
(b) perform a registration of the first and second scans;
(c) identify first lesions from disease tissue in the first scan and second lesions from disease tissue in the second scan;
(d) measure an overlapping of first regions around the first lesions with second regions around the second lesions;
(e) assign first lesions to corresponding second lesions based on a globally optimized overlap between the first and second lesions; and
(f) compare changes in corresponding first and second lesions to provide a report indicating disease progression.

It is thus a feature of at least one embodiment of the invention to better identify corresponding lesions particularly when the lesion field is crowded through the use of a global optimization process.

In some embodiments the global assignment performs a linear optimization which may employ a Munkres assignment algorithm.

It is thus a feature of at least one embodiment of the invention to provide an approach to identifying corresponding lesions that may make use of available optimization tools.

The report may identify categories of lesions as appearing, disappearing, or corresponding wherein corresponding lesions include representation of a same lesion in the first and second scans, appearing lesions are lesions in the second scan that have no corresponding lesion in the first scan, and disappearing lesions are lesions in the first scan that have no corresponding lesions in the second scan.

It is thus a feature of at least one embodiment of the invention to properly distinguish among these categories of lesions as opposed to a simple aggregate volumetric measurement allowing better understanding of variations in lesion response to treatment.

In some embodiments, the report may identify different changes in lesion volume in different lesions between the first and second scans.

It is thus a feature of at least one embodiment of the invention to provide longitudinal volume comparisons that can be specific to individual or groups of lesions that differ.

The invention may include a step of clustering lesions after step (c) to combine at least two lesions in one of the first and second scans that overlap with a single lesion in another of the first and second scans into a single lesion in the one of the first and second scans.

It is thus a feature of at least one embodiment of the invention to accommodate the fact that lesions may split and merge to provide an improved measure of lesion response without, for example, treating a split lesion as new or appearing lesions.

The combining of lesions may evaluate a separation of the several lesions compared to a dimension of the single lesion. In one embodiment, the dimension of the single lesion may be measured in relationship to an axis between centers of the several lesions, for example, where the dimension is the longest chord of the single lesion having no more than a predetermined angular separation from the axis. In some cases, the predetermined angular separation is less than 10 degrees.

It is thus a feature of at least one embodiment of the invention to provide a clustering process informed by biological processes that tend to preserve lesion asymmetries.

The region around the lesions may be a conformal region larger than the lesion.

It is thus a feature of at least one embodiment of the invention to preserve in the analysis of overlapping information about the contour of the lesion for improved analysis.

In some embodiments, the region around the lesions is dilated by at least a margin of 15 mm.

It is thus a feature of at least one embodiment of the invention to effect a trade-off between insensitivity to misregistration and inability to properly distinguish lesions in a crowded lesion field.

The scans may be molecular imaging scans.

It is thus a feature of at least one embodiment of the invention to permit informed lesion identification through knowledge of variations in biological or physiological processes associated with diseased tissue and revealed by medical imaging.

The registration may provide a three-dimensional, non-rigid registration.

It is thus a feature of at least one embodiment of the invention to work well in soft tissue outside of well-defined organs, as distinguished, for example, from analysis of skeletal disease These particular objects and advantages may apply to only some embodiments falling within the claims and thus do not define the scope of the invention.

DETAILED DESCRIPTION OF A PREFERRED EMBODIMENT

System Hardware

Figure 1:
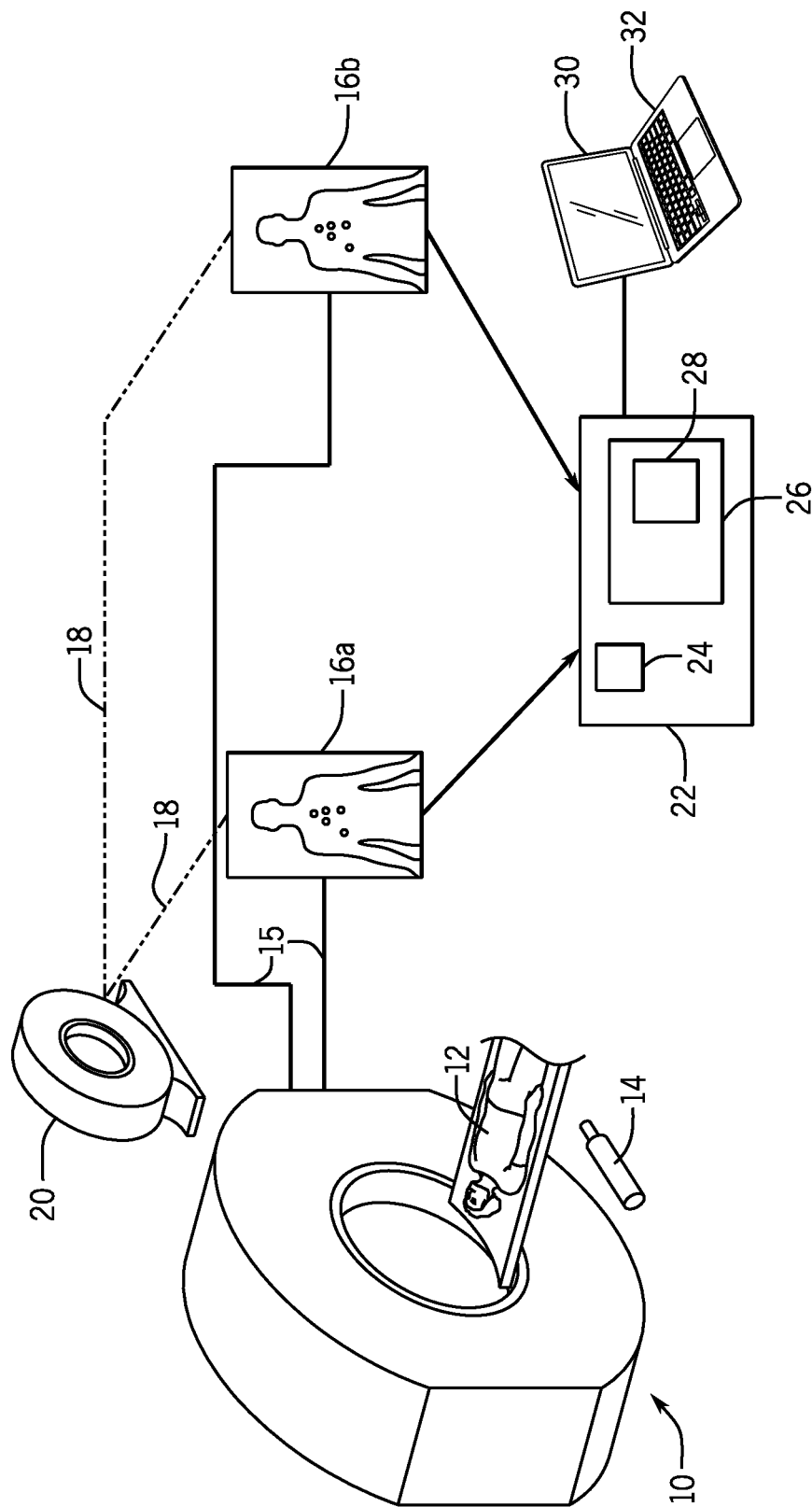
FIG. 1 is a simplified block diagram of the hardware associated with the present invention showing a scanning process for obtaining molecular (e.g., PET or SPECT) and/or anatomical (e.g., CT, MRI, or US) scans for use in practice of the present invention.

Referring now to FIG. 1, a scanner 10 capable of medical imaging from which one can identify lesions (e.g., molecular imaging) may scan a patient 12 after introduction of a contrast agent 14 (e.g., such as a radioactive tracer) into the patient 12.

The scanner 10, in one example, may be a PET (positron emission tomography) scanner. As is generally understood in the art, PET is a nuclear medical imaging technique producing three-dimensional image data revealing functional processes in the body reflected by migration of the molecular imaging agent 14 preferentially to all or part of the diseased tissue (henceforth "lesion"). The molecular imaging agent 14 in this case will be a positron emitting radio nucleotide attached to a biologically active molecule, the latter selected to participate in the lesion's metabolism.

The patient 12 may be imaged at multiple times including at least two different scans to produce molecular imaging data 15 that may be collected into two "scans" 16a and 16b, for example, scan 16a taken before and scan 16b taken after a session of treatment of the patient 12 by chemotherapy, radiation therapy, or the like. Optionally, the functional scans 16 may be supplemented with additional scans by other scanners 20, for example, a conventional kilovoltage or megavoltage CT (computed tomography), MRI (magnetic resonance imaging), or ultrasound system, such as may provide higher resolution image data 18 that presents anatomical information typically without the metabolic information. Generally, the scans 16 incorporating the image data 18 will present measures of the molecular imaging agent 14 in multiple points each associated with volume elements (voxels) distributed in three dimensions, although only two dimensions are shown for clarity.

The pre-treatment and post-treatment scans 16 may be received by an electronic computer 22 for processing as will be described in greater detail below. Generally, the electronic computer 22 includes one or more processing units 24 communicating with a memory 26 holding data and a stored program 28 for effecting portions of the present invention. The computer 22 may communicate with a graphics display 30 for displaying color output images based on the scans 16 and with user input devices 32 such as a keyboard, mouse, or the like, each allowing entry of data by user. Generally, the program display 30 will display an output indicating disease progression or regression based on measures of radiotracer uptake within multiple lesion locations in the patient 12. These measures may be based on one or both scans 16. The invention will be described with respect to tracking metastatic lesions from cancer; however, the inventors contemplate that it may also be used with a variety of cancerous and noncancerous lesions including but not limited to skin lesions, retinal vascular network abnormalities, brain lesions related to Alzheimer's disease and multiple sclerosis, various polyps and cysts, arterial calcification, inflamed lymph nodes, etc.

Programming Operation

Figure 2:
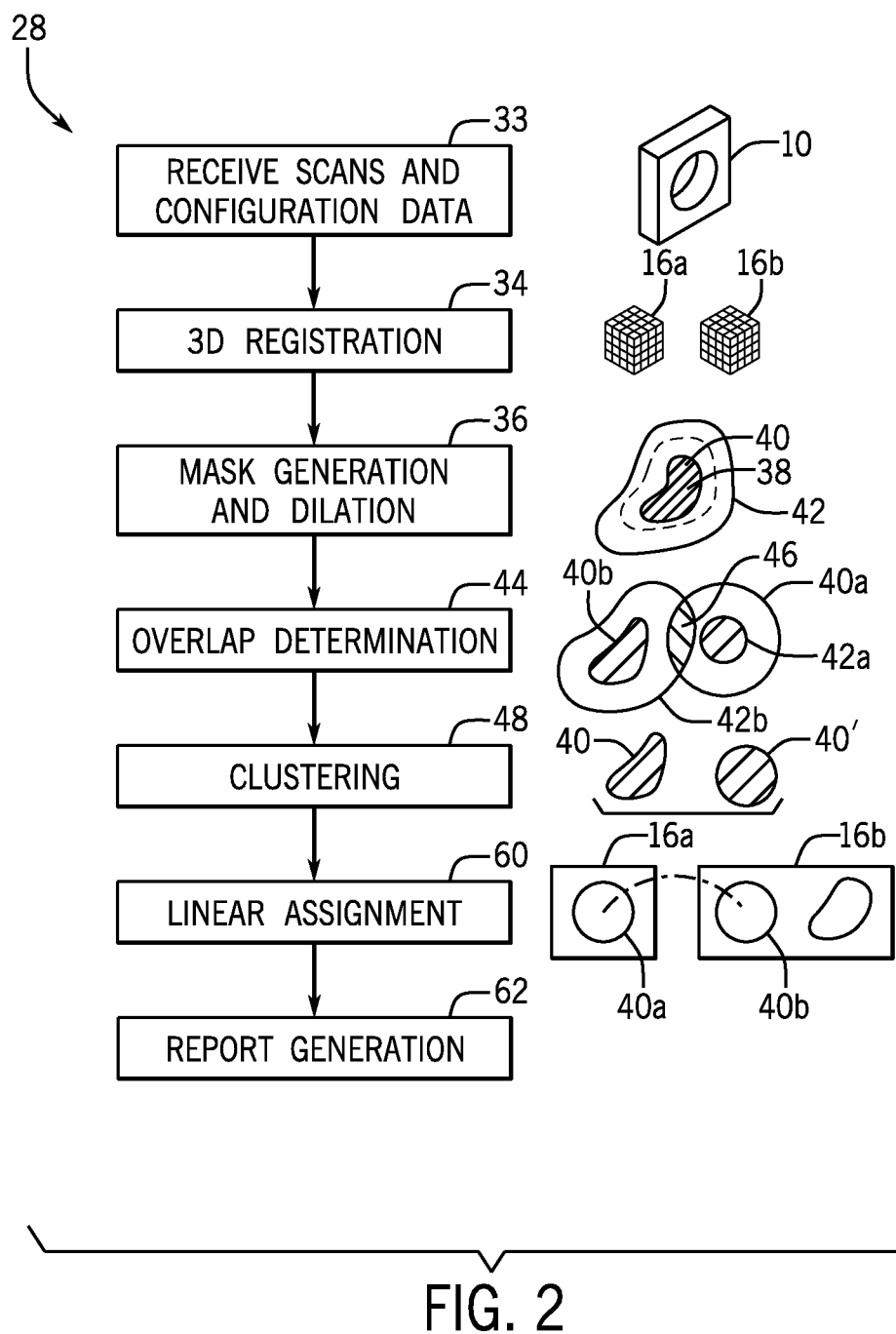
FIG. 2 is a flowchart showing principal steps in providing a quantitative measure of multiple dispersed lesion regions throughout the body of the patient.

Referring now also to FIG. 2, the program 28 may accept through input device 32 configuration information characterizing the type of cancer or other disease being treated, file names for accessing the scans 16, and an identification of the type of imaging 14 (for example, the type of molecular imaging agent being used), as indicated by process block 33. Nonlimiting examples of imaging with molecular imaging agents 14 include 18F-FLT (3'-deoxy-3'-[18F]fluoro-L-thymidine), a marker of cellular proliferation that quickly accumulates in proliferating cells that are synthesizing DNA and can be imaged with PET, and 18F-FDG (2-deoxy-2-[18F]fluoro-D-glucose). 18F-FLT and 18F-FDG can be used to image upper tract urothelial, rectal, breast, lung (non-small cell), prostate, colon, ovarian, appendiceal, adenoid, and squamous cell cancers, and metastatic melanoma.

The invention further contemplates the use of other methods of distinguishing tissue lesions from healthy tissue such as parametric diffusion maps from diffusion weighted magnetic resonance imaging (DW-MRI) imaging, single-photon emission computed tomography (SPECT) tracers, and even anatomical characterization without lesion enhancing materials.

After acquisition, the pre-treatment and post-treatment scans 16 may be registered or matched to each other using a three-dimensional registration process per process block 34. In one example, this registration may minimize a sum of square differences between voxel values in the later and the earlier scans 16a and 16b respectively, although the inventors contemplate the possibility of using other registration objective functions such as normalized mutual information and the like. The voxel values from the CT machine (or other anatomical imaging device such as an MRI machine) are preferably used over the molecular imaging data from the PET machine so as to perform an anatomical alignment independent of possible changes in the lesions. The invention also contemplates that it may be possible to do the registration in two dimensions only using these or other registration techniques.

In one example embodiment, a deformable registration may be applied to the scan 16b using free-form deformation with 3rd order B-splines interpolation and an hierarchical control grid as described in Rueckert, D., Sonoda, L. I., Hayes, C., Hill, D. L. G., Leach, M. O., Hawkes, D. J., 1999, "Nonrigid registration using free-form deformations: application to breast MR images", IEEE Trans., Med. Imaging 18, 18:712-21 hereby incorporated by reference. The resulting registration provides a transformation field T that will be applied to a binary lesion mask obtained from the later scan 16b as discussed below.

Referring still to FIG. 2, at succeeding process block 36 a three-dimensional binary lesion mask 38 may be prepared for each of scans 16a and 16b representing a lesion 40, for example, at each voxel with a value of "1" and the absence of a lesion with a "0." As noted, the scans 16 provide a set of data points representing molecular imaging agent uptake at three dimensionally dispersed voxels throughout the patient 12. One method of generating the binary lesion mask 38 may evaluate the molecular imaging uptake values within the regions 42 against a threshold, for example, of just above background uptake levels. Voxels of the patient 12 having the molecular imaging agent uptake values above the threshold 52 may then be identified as lesions 40. Other identification techniques are contemplated including, for example, uptake gradient-based methods or imaging feature-identifying methods. After the binary lesion mask 38 is developed for scan 16b, the transformation field T discussed above is applied to that mask 38 so that the masks for scan 16a and 16b are approximately registered.

The identified lesions 40 of the binary lesion masks 38 may then be dilated or expanded, for example, by a morphological mathematical dilation which expands the boundaries of the periphery of the lesion 40 by a predetermined margin in one or more successive iterations. Importantly, this dilation is conformal and does not assume a spherical lesion but follows actual lesion outer surfaces. In one embodiment, the dilation is between 25 mm and 30 mm, and desirably between 15 mm and 40 mm. In some embodiments, the dilation may not be uniform in all directions (e.g. spherical) but may be relatively longer along particular anatomical directions which lesions are known to follow (e.g., breast ducts) or limited by tissue where lesions would not be expected, for example, by bone or other anatomical structures (e.g., skull, other bone).

This dilation is performed on both of scans 16a and 16b to create an expanded region 42 about the lesions 40 in each scan 16. The regions 42 define an overlap 46 between corresponding regions 42 in different of the scans 16a and 16b. The amount of dilation controls the overlap 46 and thus sets the ability of the system to identify misregistered but nevertheless corresponding lesions 40 (that is, the same lesion in different scans 16a and 16b) and may be adjusted as guided by this principle. In one embodiment, the amount of dilation may be changed dynamically in different portions of the scans 16 according to a local density of lesions 40 (how many lesions per volume) increasing dilation when there is lower density. For example, the density may be computed to define a spherical region being a predetermined multiple, for example, five, of the diameter of a sphere encompassing the lesion 40 to be dilated.

Referring still to FIG. 2, at succeeding process block 44, amounts of overlap 46 for each lesion 40 in scan 16a and every lesion 40 in scan 16b are compiled. This information may be recorded, for example, in a logical matrix M of dimensions N×N where N is the largest number of lesions identified in the scan 16a or 16b and each matrix element $M_{i,j}$ describes the cardinality in the intersection of the regions 42 numerically identified by the subscripts i and j ("i" being identification number of the lesions 40 in scan 16a and "j" being an arbitrary identification number of the lesions 40 in scan 16b). The cardinality of the intersection is most simply the number of voxels in the overlap 46.

At succeeding process block 48, the possibility that lesions have merged or split between scans 16a and 16b is addressed through a clustering operation which links otherwise separate lesions 40 and 40' in a single given scan 16a or 16b as one lesion 40. The clustering operation separately considers each scan 16a (for merging lesions 40) and scan 16b (for separating lesions 40).

Figure 3:
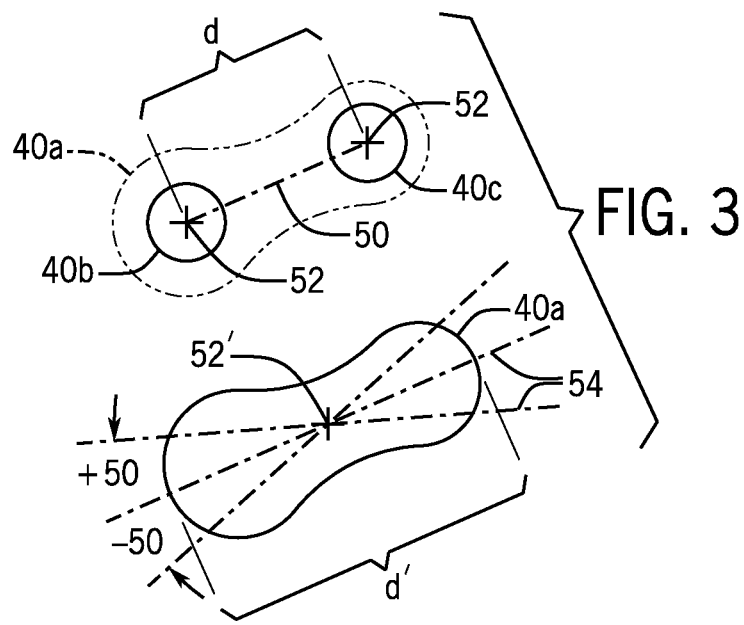
FIG. 3 is a graphic representation of a process of clustering lesions used in one embodiment of the invention and showing relevant dimensions and axes.

Referring now to FIG. 3, clustering for lesions 40 in either scan is limited to an analysis of lesions 40 in a first scan that overlap with a common lesion in the other scan. For example, lesions 40b and 40c in later scan 16b (here represented for clarity by their regions 42), may be linked by their overlap with lesion 40a in the earlier scan 16a and thus considered for clustering. In the clustering process, an axis 50 is defined between centroids 52 of the lesions 40b and 40c and a distance d determined between those centroids 52. A corresponding distance d' is then developed on lesion 40a (duplicated and displaced from lesions 40b and 40c in FIG. 3 for clarity) being the longest chord through the centroid 52' of lesion 40a evaluated over a range of angles of an axis 54 having a center position parallel to axis 50 and range extremes at predetermined angular deviations from that center position (cones having an apex angle equal to twice the angular deviation and centered on the axis 50). In one embodiment the range of angles may be plus or minus 5 degrees. If the length of d is smaller than d', the lesions 40b and 40c are clustered to be a single logical lesion for subsequent analysis. Note that as described, this process operates both for lesions 40 that are splitting and combining between the scans 16a and 16b. In the case where there are more than one lesion, the axis 50 may be a line fit to the centroids 52, for example by the least-squares method Referring again to FIG. 2 and process block 60, the lesions 40 are then renumbered in an arbitrary but lesion-unique sequence and matrix M described above reconstructed with the overlap 46 now considering the union of the clustered lesions 40 and 40' in one scan 16 with respect to the number of voxels in the overlap 46 with a lesion in the other scan 16. The lesions 40 as so defined by the clustering are now analyzed to identify corresponding lesions between scans 16a and 16b. Importantly, this association of the lesions 40 in the different scans 16a and 16b employs a non-greedy global process to greatly improve the optimization.

In one embodiment, the matrix M (as adjusted to accommodate the clustering described above) is used to develop a cost matrix C where $C_{i,j}=1/M_{i,j}$ (reflecting a desire to maximize overlap among lesions 40), and this cost matrix is used to solve a linear assignment problem of lesions 40 in scan 16a to lesions 40 and scan 16b. In one embodiment this process may follow the techniques described in Jaqaman, K., Loerke, D., Mettlen, M., Kuwata, H., Grinstein, S., Schmid, S. L., Danuser, G., 2008, "Robust single-particle tracking in live-cell time-lapse sequences", Nat. Methods 5, 695-702 hereby incorporated by reference. Generally, the result is that the amount of overlap 46 between corresponding lesions is globally maximized under the constraint that a given lesion 40 in one scan 16 may only correspond to a single lesion in the second image 16b.

Figure 4:
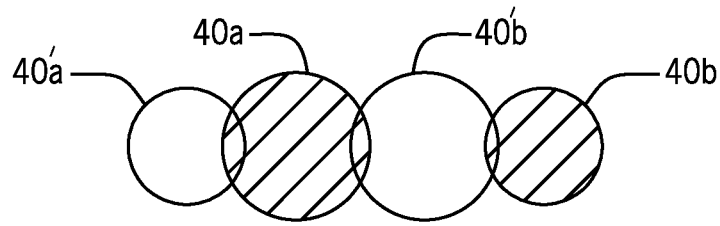
FIG. 4 is a simplified diagram of overlapping lesions that can be correctly isolated by a global process.

Referring now to FIG. 4, using this process lesions 40a and 40b from scan 16a, may be properly matched with lesions 40'a and 40'b respectively from scan 16b rather than, for example, lesion 40a being matched to both lesions 40'a and 40'b such as might occur with a greedy algorithm matching.

Figure 5:
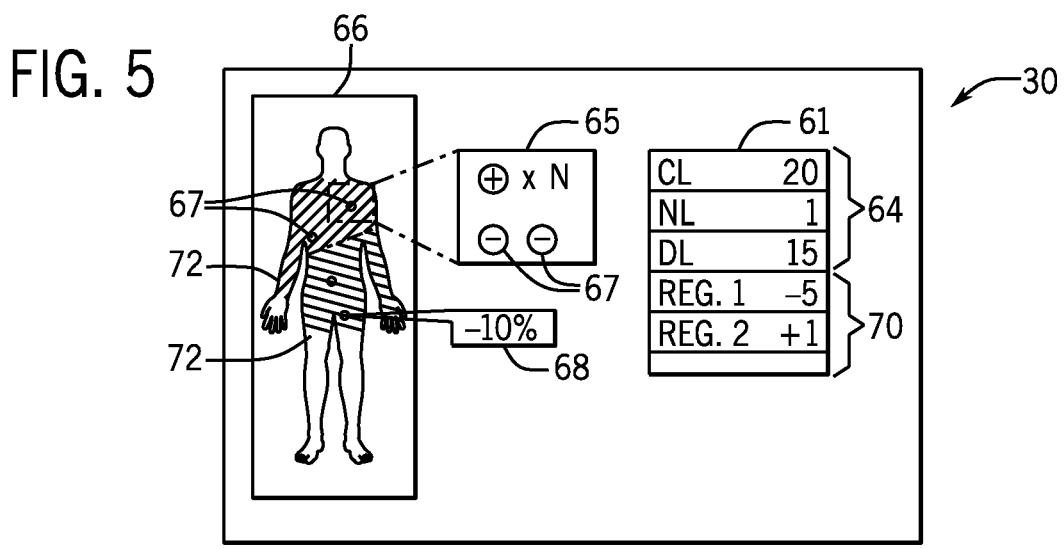
FIG. 5 is a representation of a screen display providing a report possible with the present invention.

At succeeding process block 62 and referring also to FIG. 5, the resulting identification of corresponding lesions 40 among scans 16a and 16b allows each lesion 42 be identified as a corresponding lesion (having counterparts in both scans 16a and 16b) or an appearing lesion existing in scan 16b but having no counterpart in scan 16a or a disappearing lesions 40 having an instance in scan 16a but no corresponding lesion in scan 16b. This information can be provided in a report 61, for example, on display 30 in the form of a chart depicting quantitatively the number of lesions in each of these categories as indicated by chart entries 64. Importantly, each lesion (corresponding, appearing, or disappearing) may also be marked on an image 66 of the patient (or a movable magnified portion 65) with a unique symbol 67 (e.g., "x" for disappearing lesions, "n" for appearing lesions, and a circle for corresponding lesions) developed from one or more of the scans 16a or 16b so that the physician can gain an understanding of any trend associated with lesions in a particular area or region with respect to treatment efficacy in those regions, for example, in regions having a greater number of disappearing lesions. Individual lesions (displayed in magnified view in a pop-up 68 associated with an individual lesion 40) or groups of lesions defined by areas (shown in chart area 70) may also be tracked quantitatively and on the image with respect to whether there has been a decrease or increase in lesion volume (for example, with a plus or minus sign). More generally shaded region areas 72 can be applied to the image 66 providing a mathematical generalization of those regions with respect to increase or decrease in lesion volume of the lesions in those regions, for example, red showing an increase in lesion volume and green showing a decrease in lesion volume.

In other embodiments, the report may also provide information about maximum uptake value, average uptake value, sum total uptake value of the contrast agent.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to an electronic computer can be understood to include one or more computers that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

What we claim is:

1. An apparatus for assessing treatment of a patient comprising:
an electronic computer executing a stored program to:
(a) receive a first and a subsequent, second scan of tissue of the patient revealing diseased tissue at different times with respect to treatment of the patient, the first and subsequent second scan including at least one lesion that merges or splits between the first and second subsequent scan;
(b) perform a registration of the first and second scans;
(c) identify first lesions in the first scan and second lesions in the second scan;
(d) measure an overlapping of first regions around the first lesions with second regions around the second lesions;
(e) globally assign first lesions to corresponding second lesions based on a global optimization of assignment according to overlap between the first and second regions to identify lesions of the first and second scans that have split or merged; and
(f) compare changes in corresponding first and second lesions as identified to provide a report indicating disease progression.

2. The apparatus of claim 1 wherein the assignment performs a linear optimization.

3. The apparatus of claim 2 wherein the assignment employs a Munkres assignment algorithm.

4. The apparatus of claim 1 wherein the report identifies categories of lesions as appearing or disappearing or corresponding wherein corresponding lesions include a representation of a same lesion in the first and second scans, appearing lesions are lesions in the second scan that have no corresponding lesion in the first scan, and disappearing lesions are lesions in the first scan that have no corresponding lesions in the second scan.

5. The apparatus of claim 1 wherein the report identifies changes in lesion volume and different lesions between the first and second scans.

6. The apparatus of claim 1 wherein the region is larger than the lesion and conformal to the lesion.

7. The apparatus of claim 6 wherein the region is dilated by at least a margin of 15 mm.

8. The apparatus of claim 6 wherein the region is dilated by a margin that is functionally related to a density of lesions in a predetermined area about the region.

9. The apparatus of claim 1 wherein scans are molecular imaging scans.

10. The apparatus of claim 1 wherein registration provides a nonrigid registration three-dimensional registration.

11. An apparatus for assessing treatment of a patient comprising:
　　an electronic computer executing a stored program to:
　　(a) receive a first and a subsequent, second scan of tissue of the patient revealing diseased tissue;
　　(b) perform a registration of the first and second scans;
　　(c) identify first lesions in the first scan and second lesions in the second scan;
　　(d) measure an overlapping of first regions around the first lesions with second regions around the second lesions;
　　(e) globally assign first lesions to corresponding second lesions based on a global optimization of overlap between the first and second regions; and
　　(f) compare changes in corresponding first and second lesions to provide a report indicating disease progression;

further including the step of clustering lesions after step (c) to combine at least two lesions in one of the first and second scans that overlap with a single lesion in another of the first and second scans into a single lesion in one of the first and second scans.

12. The apparatus of claim 11 wherein the combining evaluates a separation of the at least two lesions compared to a dimension of the single lesion.

13. The apparatus of claim 12 wherein the dimension of the single lesion is measured in relationship to an axis between centers of the at least two lesions.

14. The apparatus of claim 13 wherein the dimension is a longest chord of the single lesion having no more than a predetermined angular separation from the axis.

15. The apparatus of claim 14 wherein the predetermined angular separation is less than 10 degrees.

16. A method for assessing cancer treatment of a patient comprising:
　　(a) receiving a first and subsequent second scan of tissue of the patient identifying diseased tissue and revealing the diseased tissue at different times with respect to treatment of the patient, the images including lesions that have split or merged;
　　(b) performing a global registration of the first and second scans
　　(c) identifying first lesions in the first scan and second lesions in the second scan;
　　(d) measuring an overlapping of regions around the first lesions with regions around the second lesions;
　　(e) globally assigning first lesions to corresponding second lesions based on a global optimization of assignment according to overlap between corresponding first and second lesions to identify lesions of the first and second scans that have split or merged; and
　　(f) comparing the changes in corresponding first and second lesions as identified to provide a report indicating disease progression.

* * * * *